(12) United States Patent
Jan et al.

(10) Patent No.: US 7,812,205 B2
(45) Date of Patent: Oct. 12, 2010

(54) LAYERED ZEOLITIC CATALYST FOR IMPROVED LINEARITY IN DETERGENT ALKYLATION

(75) Inventors: Deng-Yang Jan, Elk Grove Village, IL (US); Mark G. Riley, Hinsdale, IL (US)

(73) Assignee: UOP LLC, Des Plaines, IL (US)

( * ) Notice: Subject to any disclaimer, the term of this patent is extended or adjusted under 35 U.S.C. 154(b) by 467 days.

(21) Appl. No.: 11/871,600

(22) Filed: Oct. 12, 2007

(65) Prior Publication Data

US 2009/0099399 A1    Apr. 16, 2009

(51) Int. Cl.
*C07C 2/66* (2006.01)
(52) U.S. Cl. ....................... 585/467; 585/455
(58) Field of Classification Search .......... 585/467, 585/455
See application file for complete search history.

(56) References Cited

U.S. PATENT DOCUMENTS

| 5,043,508 | A | 8/1991 | Aufdembrink et al. |
| 5,105,042 | A | 4/1992 | Aufdembrink et al. |
| 6,051,521 | A | 4/2000 | Cheng et al. |
| 6,060,632 | A | 5/2000 | Takamatsu et al. |
| 6,187,981 | B1 | 2/2001 | Marinangeli et al. ........ 585/323 |
| 6,376,730 | B1 | 4/2002 | Jan et al. .................... 585/467 |
| 6,448,458 | B1 | 9/2002 | Marinangeli et al. .......... 585/24 |
| 6,515,169 | B1 | 2/2003 | Marinangeli et al. .......... 562/93 |
| 6,589,927 | B1 | 7/2003 | Kott et al. ................... 510/357 |
| 6,710,003 | B2 | 3/2004 | Jan et al. ..................... 502/60 |
| 2002/0082460 | A1* | 6/2002 | Verduijn et al. ............. 585/475 |

FOREIGN PATENT DOCUMENTS

WO    WO 02/41990 A1    5/2002

* cited by examiner

*Primary Examiner*—Thuan Dinh Dang
(74) *Attorney, Agent, or Firm*—Arthur E Gooding

(57) ABSTRACT

A process is disclosed wherein a layered catalyst is used for the alkylation of benzene with a substantially linear olefin. The layered catalyst allows for shifting the operating conditions to increase the alkylation of benzene, while reducing the amount of isomerization of the alkyl group. This is important for increasing the quality of the alkylbenzene by increasing the linearity of the alkylbenzene.

9 Claims, 1 Drawing Sheet

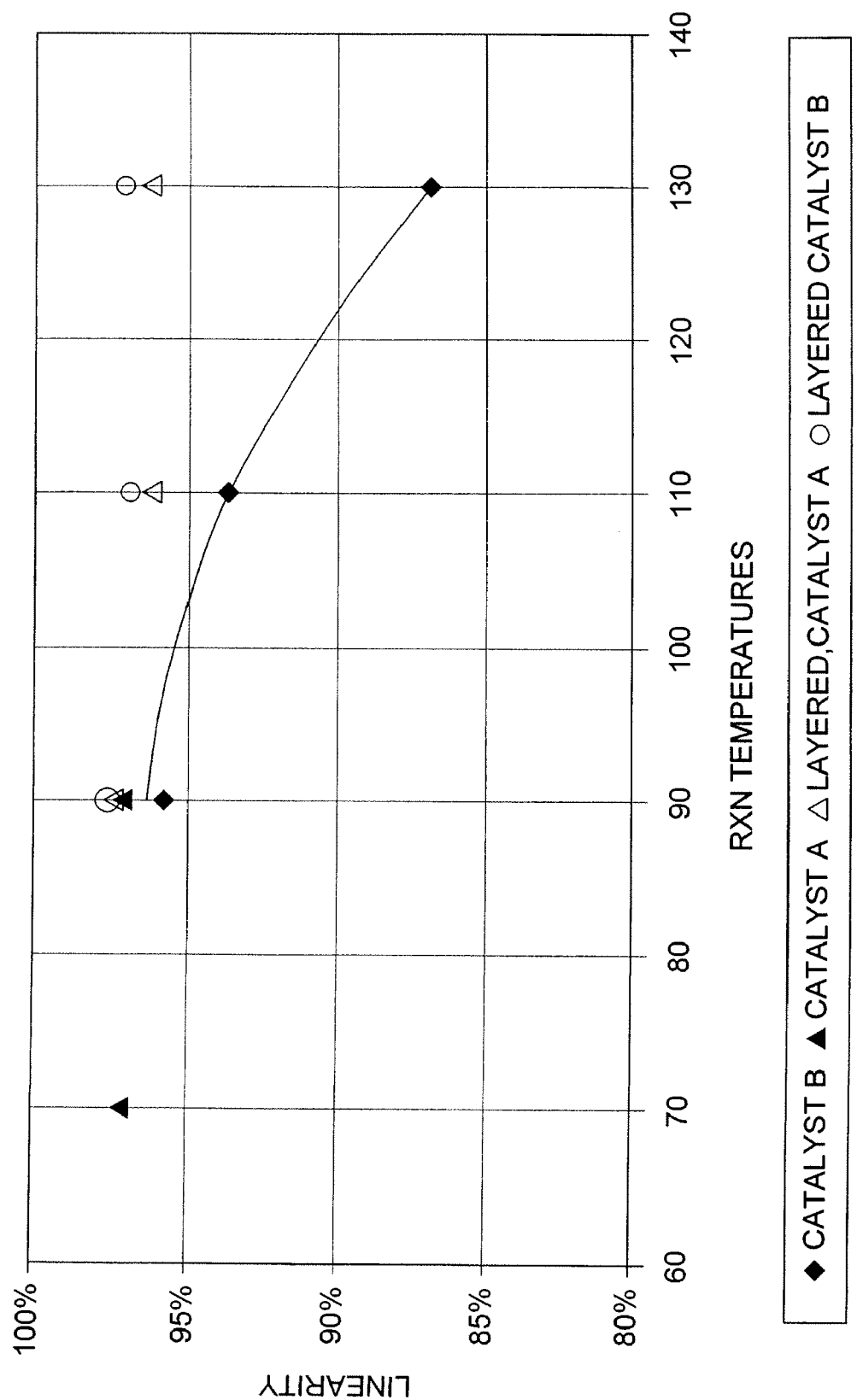

LAYERED ZEOLITIC CATALYST FOR IMPROVED LINEARITY IN DETERGENT ALKYLATION

FIELD OF THE INVENTION

The present invention relates to the production of an arylalkane. In particular, this relates to an aromatic alkylation process using a layered catalyst for improved linearity in the alkylated product.

BACKGROUND OF THE INVENTION

The alkylation of aromatic hydrocarbons such as benzene is a well-developed art, and one that is practiced commercially using solid catalysts in large scale industrial units. The alkylation of benzene with olefins having from 8 to 28 carbons produces alkylbenzenes that have various commercial uses. One use is to sulfonate the alkylbenzenes to produced sulfonated alkylbenzenes for use at detergents. Alkylbenzenes are produced as a commodity product for detergent production, often in amounts from 50,000 to 200,000 metric tones per year per plant. The alkylation process occurs by reacting benzene with an olefin in the presence of a catalyst at an elevated temperature and pressure.

The performance of aromatic alkylation processes is characterized to a significant extent by the activity and selectivity of the catalyst in the operating environment of the process. Currently available catalysts for aromatic alkylation include those having considerable acidity such as aluminum chloride and zeolites. The characterization of solid materials in terms their acidic properties is described in detail in Satterfield, Heterogeneous Catalysis in Practice, McGraw-Hill, pp. 151-153.

Alkylbenzene, when used for detergents, must meet stringent product specifications to be commercially acceptable. The production of alkylbenzene usually produces a mixture of linear and branched alkylbenzenes. However, due to the lower biodegradability of branched alkylbenzenes, the marketplace transitioned to almost exclusively using linear alkylbenzenes in the production of detergents as they produced a product that was environmentally more acceptable in its relative quickness to biodegrade. One of the problems associated with the production of linear alkylbenzenes is the isomerization of the alkyl group during the production, and therefore reducing the quality of the product. Understanding the reactions that take place and controlling the reaction environment can produce a higher quality product with lower loss of raw materials.

SUMMARY OF THE INVENTION

The invention provides a process for the production of linear alkylbenzenes from a substantially linear olefin having from 8 to 28 carbon atoms with an aromatic hydrocarbon feedstream in the presence of a catalyst under reaction conditions. The catalyst in the present process comprises a layered composition having an inner core, and an outer layer bonded to the inner core, wherein the outer layer comprises a molecular sieve and a binder.

Other objects, advantages and applications of the present invention will become apparent to those skilled in the art from the following detailed description and drawing.

BRIEF DESCRIPTION OF THE DRAWING

FIGURE shows results of the layered catalyst versus the catalyst as a whole extrudate.

DETAILED DESCRIPTION OF THE INVENTION

An embodiment of the present invention is a process that uses two feedstocks, a substantially linear (non-branched) olefin and an aryl compound. The linear olefin can be a mixture of linear olefins with double bonds at terminal and internal positions or a linear alpha olefin with double bonds located at terminal positions. Preferably the aryl compound is benzene. The linear olefin comprises a molecule having from 8 to 28 carbon atoms, preferably from 8 to 15 carbon atoms, and more preferably from 10 to 14 carbon atoms. The olefin and aryl compounds are reacted in the presence of a catalyst under reaction conditions. The catalyst comprises a layered composition having an inner core and an outer layer bonded to the inner core. The outer layer includes a molecular sieve and a binder.

The reaction conditions for alkylation are selected to minimize isomerization of the alkyl group and minimize polyalkylation of the benzene, while trying to maximize the consumption of the olefins to maximize product. Alkylation conditions include a reaction temperature between 50° C. to 200° C., and preferably between 80° C. to 175° C. The pressures in the reactor are from 1.4 MPa (203 psia) to 7 MPa (1015 psia), and preferably from 2 MPa (290 psia) to 3.5 MPa (507 psia). To minimize polyalkylation of the benzene, the aryl to monoolefin molar ratio is between 2.5:1 to 50:1, and preferably between 5:1 to 35:1. The average residence time in the reactor helps control product quality, and the process is operated at a liquid hourly space velocity (LHSV) from 0.1 to 30 $hr^{-1}$, with a preferred LHSV between 0.3 to 6 $hr^{-1}$.

The olefins can be produced from the dehydrogenation of paraffins, cracking of paraffins and subsequent oligomerization of smaller olefinic molecules, or other known processes for the production of linear monoolefins. The separation of linear paraffins from a mixture comprising normal paraffins, isoparaffins and cycloparaffins for dehydrogenation can include the use of known separation processes, such as the use of UOP Sorbex separation technology. UOP Sorbex technology can also be used to separate linear olefins from a mixture of linear and branched olefins.

A method for the production of the paraffinic feedstock is the separation of linear (nonbranched) hydrocarbons or lightly branched hydrocarbons from a kerosene boiling range petroleum fraction. Several known processes that accomplish such a separation are known. One process, the UOP MoleX™. process, is an established, commercially proven method for the liquid-phase adsorption separation of normal paraffins from isoparaffins and cycloparaffins using the UOP Sorbex separation technology.

Paraffins can also be produced in a gas to liquids (GTL) process, where synthesis gas made up of CO and H2 at a controlled stoichiometry are reacted to form larger paraffinic molecules. The resulting paraffinic mixture can then be separated into normal paraffins and non-normal paraffins, with the normal paraffins dehydrogenated to produce substantially linear olefins.

In the process of producing olefins from paraffins, by products include diolefins and alkynes, or acetylenes. The streams comprising diolefins and acetylenes are passed to a selective hydrogenation reactor, where the diolefins and alkynes are converted to olefins.

Alkylbenzenes are used as a base chemical for surfactant based detergents. The alkylbenzenes are typically sulfonated to produce the surfactants. However, branched alkylbenzenes have poor biodegradability and create foam in rivers and lakes where the detergents wash into. Having a biodegradable detergent has a less adverse affect on the environment and linear alkylbenzenes are much more biodegradable and consequently have a lower environmental impact. Reducing the amount of branching produces a higher quality base product for use in detergents.

The present process uses two feedstocks, a substantially linear (non-branched) olefin and an aryl compound. The linear olefin can be an olefin with internal and terminal double bonds or alpha olefin with double bonds located at the terminal positions. Preferably the aryl compound is benzene. The linear olefin comprises a molecule having from 8 to 28 carbon atoms, preferably from 8 to 15 carbon atoms, and more preferably from 10 to 14 carbon atoms.

In detergent alkylation, skeletal isomerization of the olefin is kinetically controlled and not desirable. As a result, skeletal isomerization is sensitive to operating conditions such as temperature and relative amounts of catalyst in the reactor. In contrast, alkylation is predominantly diffusion controlled and thus not as sensitive to the relative amounts of catalyst as the isomerization reaction in the reactor. By layering the catalyst, the isomerization can be suppressed without sacrificing the alkylation performance. This improves the linearity of the alkylbenzene which is one measure of LAB product quality, i.e. greater linearity is perceived as higher quality. In addition, the operating temperatures are allowed to increase to improve catalyst reactivity, and stability, while maintaining product linearity.

By "skeletal isomerization" of an alkyl group, it is meant isomerization that increases the number of primary carbon atoms of the alkyl group. The skeletal isomerization of the alkyl group increases the number of methyl group branches of the aliphatic alkyl chain. Because the total number of carbon atoms of the alkyl group remains the same, each additional methyl group branch causes a corresponding reduction by one of the number of carbon atoms in the aliphatic alkyl chain.

The preferred catalyst comprises an inner core composed of a material which has substantially lower isomerization reactivity relative to the outer layer. Some of the inner core materials are also not substantially penetrated by liquids Examples of the inner core material include, but are not limited to, refractory inorganic oxides, silicon carbide, and metals. Examples of refractory inorganic oxides include without limitation alpha alumina, cordierite, magnesia, metals, silicon carbide, theta alumina, titania, zirconia, and mixtures thereof. Preferred inorganic oxides are alumina of various crystalline phases and cordierite.

The materials which form the inner core can be formed into a variety of shapes such as pellets, extrudates, spheres, or irregularly shaped particles, although not all materials can be formed into each shape. Preparation of the inner core can be done by means known in the art such as oil dropping, pressure molding, metal forming, pelletizing, granulation, extrusion, rolling methods, and marumerizing. A spherical inner core is preferred. The inner core whether spherical or not has an effective diameter of 0.05 mm (0.0020 in) to 5 mm (0.2 in) and preferably from 0.8 mm (0.031 in) to 3 mm (0.12 in). For a non-spherical inner core, effective diameter is defined as the diameter the shaped article would have if it were molded into a sphere. Once the inner core is prepared, it is calcined at a temperature of from 400° C. (752° F.) to 1800° C. (3272° F.). When the inner core comprises cordierite, it is calcined at a temperature of from 1000° C. (1832° F.) to 1800° C. (3272° F.).

The outer layer of the catalyst is applied by forming a slurry of the molecular sieve material and then coating the inner core with the slurry by means known in the art. It is preferred that the slurry includes an organic bonding agent which aids in the adhesion of the molecular sieve material to the inner core. Examples of the organic bonding agent include, but are not limited to, polyvinyl alcohol (PVA), hydroxy propyl cellulose, methyl cellulose, and carboxy methyl cellulose. The bonding agent, which is present in the slurry in an amount between 0.1 wt % and 3 wt % is consumed during the calcination of the catalyst. The outer layer further includes a binder that is resistant to temperature and reaction conditions while providing hardness and attrition resistance.

Molecular sieves useful in the present invention include, but are not limited to, zeolites such as UZM-8, Faujasite, beta, MTW, MOR, LTL, MWW, EMT, UZM-4 and mixtures thereof. UZM-4 is a silica alumina version of the BPH structure and has the substantial acidity needed for the alkylation reaction. The binders used are inorganic metal oxides and examples include, but are not limited to, alumina, silica, magnesia, titania, zirconia, and mixtures thereof.

Coating the inner core with the slurry can be done by means known in the art, such as rolling, dipping, spraying, etc. One preferred technique is to spray the slurry into a fluidized bed of inner core particles. This procedure coats the particles in a fairly uniform manner and provides for a thickness of the layer from between 10 and 300 micrometers. The thickness is controlled by time and other operating parameters. The coated particles are then dried at a temperature from 100° C. (212° F.) to 300° C. (572° F.) for a time from 1 to 24 hours and then calcined at a temperature from 400° C. (752° F.) to 900° C. (1652° F.) for a time from 0.5 to 10 hours to effectively bond the outer layer to the inner core and provide a layered catalyst. For operating efficiency, the drying and calcining steps can be combined into one step.

Zeolite Y's used for layering are obtained from modifications of as synthesis Y with $SiO_2/Al_2O_3$ molar ratio of 4.0 and $Na_2O/Al_2O_3$ molar ratio of 1.0. Zeolite Y-84 was prepared by first ammonium ion exchange as synthesized Y to replace approximately 75% of the sodium with ammonium, steamed at 600 C and then ammonium ion exchanged with the rest of the sodium. The $SiO_2/Al_2O_3$ of Y-84 is comparable to that of a synthesized Y. Zeolite Y-85 was prepared using the same procedure as Y-84 with the exception that the last ammonium exchange was conducted in the presence of nitric acid. The $SiO_2/Al_2O_3$ molar ratio of Y-85 ranges from 6.5 to 27. The sample used for the layering has a $SiO_2/Al_2O_3$ molar ratio of 8.5. Zeolite RSN-Y was prepared by first ion exchanging the as synthesized Y with rare earth ions, followed by steaming at a temperature of 600° C. and then ammonium ion exchanged to reduce the sodium to minimal levels. The $SiO_2/Al_2O_3$ ratio of RSN-Y is comparable to that of as synthesized Y and contains and has a sodium content of 0.16 wt % on a volatile-free basis.

Pseudoboemite alumina, organic additive polyvinylalcohol (PVA) in combination with zeolites Y-84, Y-85 and RSN-Y, respectively, were mixed with de-ionized water to obtain slurries with solid contents ranging from 10 to 25 wt %. The resulting slurries were made up of 70 wt % zeolite and 30 wt % $Al_2O_3$ with PVA to $Al_2O_3$ ratio of 0.06 and were then sprayed into a chamber where the spheres of inner core chi-alumina were fluidized. The resulting layered catalysts were then dried at 250° C. and then calcined at 600° C. for 1 hour, and are designated as Catalysts A, B, C and D in Table 1. The same set of zeolite was also formulated into an extrudate consisting of 80 wt % zeolite and 20 wt % $Al_2O_3$ and having a diameter of 1.6 mm with a length to diameter ratio of 3. These catalyst were designated as Catalysts E, F and G and are served as comparative examples to illustrate the performance advantages of Catalysts A-D of the invention.

Catalysts A through G were evaluated for their benzene alkylation with linear olefins. The linear olefins used in the tests have carbon numbers ranging from 10 through 14, and make up about 10% olefin with the balance being the corresponding linear paraffin with an overall benzene to olefin molar ratio of 30. In a typical experiment, 46.3 grams of feed blend containing benzene and linear olefin in paraffin are weighted into an autoclave. The autoclave is purged with $N_2$ and pressurized to 2.44 MPa (340 psig $N_2$) and then heated to the target reaction temperatures. After one hour at the reaction temperature, the reactor was cooled and the products were analyzed for its composition.

Results from experiments run using the layered catalyst and comparison with a non-layered whole extrudate are shown in Table 1 and the FIGURE. As the temperatures increased for the whole extrudate, the linearity of the alkylbenzene declined. For a non-layered catalyst, in order to produce a high linearity, the reaction must be run at a relatively low temperature which reduces the reaction rate. Using a layered catalyst, the linearity was substantially maintained over a wide range of temperatures. This allows for improving the reaction rate of the alkylation reaction, more flexibility in designing the commercial units, significantly longer process cycle (higher on-stream efficiency) and longer overall catalyst stability.

lated aromatic hydrocarbon, where the catalyst comprises a layered composition consisting of an inner core, and an outer layer bonded to the inner core, wherein the outer layer comprises a zeolite selected from the group consisting of UZM-8, Faujasite, beta, MTW, MOR, LTL, MWW, EMT, BPH/UZM-4 and mixtures thereof, and a binder, and where the olefin has from 8 to 28 carbon atoms, wherein the inner core consists of a material selected from the group consisting of cordierite, alpha alumina, theta alumina, magnesia, silicon carbide, metals, zirconia, titania, and mixtures thereof, and having a substantially lower isomerization reactivity relative to the material in the outer layer and the inner core

TABLE 1

Results of Y-84 and Y-85 over an inert alumina core

| | Catalysts | | | | | |
|---|---|---|---|---|---|---|
| Description | A Layer | B Layer | A Layer | B Layer | A Layer | B layer |
| Composition | Y-84 (70/30) | Y-85 (70/30) | Y-84 (70/30) | Y-85 (70/30) | Y-84 (70/30) | Y-85 (70/30) |
| Zeolite layer thickness, microns | 94 | 132 | 94 | 132 | 94 | 132 |
| Reactor inlet target, ° C. | 130 | 130 | 110 | 110 | 90 | 90 |
| Conversion by Br # | 99.96 | 99.96 | 99.93 | 99.91 | 99.84 | 99.91 |
| Total LAB | 91.64 | 92.35 | 91.89 | 91.79 | 92 | 92.2 |
| Non-linear + quats | 3.77 | 3 | 3.82 | 3.2 | 3.5 | 3.19 |
| Total | 100 | 100 | 100 | 100 | 100 | 100 |
| 2-phenyl/LAB, % | 18.71 | 18.53 | 18.62 | 18.3 | 18.5 | 18.22 |
| Linearity, % | 96.05 | 96.85 | 96.01 | 96.63 | 96.34 | 96.66 |
| LAB/(LAB + HAB), % | 97.25 | 97.23 | 97.45 | 96.82 | 97.16 | 97.19 |
| Total alkylate | 95.41 | 95.35 | 95.71 | 94.99 | 95.5 | 95.49 |
| 2-ph/total alkyl, % | 18.0 | 17.9 | 17.9 | 17.7 | 17.8 | 17.6 |
| HAB/(LAB + AB + HAB), % | 2.6 | 2.7 | 2.4 | 3.1 | 2.7 | 2.7 |
| cracking | 2.07 | 2.04 | 1.89 | 2 | 1.81 | 1.84 |

| | Catalysts | | | | | | |
|---|---|---|---|---|---|---|---|
| Description | C Layer | D Layer | F Extrudate | F Extrudate | F Extrudate | F Extrudate | G Extrudate |
| Composition | Y-85 (70/30) | RSN Y-54 (70/30) | Y-84 (80/20) | Y-85 (80/20) | Y-85 (80/20) | Y-85 (80/20) | RSN-Y-54 (80/20) |
| Zeolite layer thickness, microns | 244 | 77 | 800 | 800 | 800 | 800 | 800 |
| Reactor inlet target, ° C. | 90 | 90 | 90 | 90 | 110 | 130 | 110 |
| Conversion by Br # | 99.91 | 99.87 | 99.9 | 99.93 | 99.9 | 99.9 | 99.80 |
| Total LAB | 92.42 | 89.14 | 92.7 | 91.26 | 88.8 | 8.02 | 90.18 |
| Non-linear + quats | 3.25 | 3.07 | 3.3 | 3.67 | 6.0 | 12.1 | 2.14 |
| Total | 100 | 100 | 100 | 100 | 100 | 100 | 100 |
| 2-phenyl/LAB, % | 18.39 | 17.29 | 17.7 | 22.12 | 27.0 | 31.7 | 17.29 |
| Linearity, % | 96.60 | 96.67 | 96.6 | 96.13 | 93.7 | 86.9 | 97.68 |
| LAB/(LAB + HAB), % | 97.38 | 93.74 | 97.7 | 96.81 | 96.8 | 95.3 | 93.86 |
| Total alkylate | 95.67 | 92.21 | 96.0 | 94.93 | 94.7 | 92.3 | 92.32 |
| 2-ph/total alkyl, % | 17.8 | 16.7 | 17.1 | 21.3 | 25.3 | 27.5 | 16.9 |
| HAB/(LAB + AB + HAB), % | 2.5 | 6.1 | 2.2 | 3.1 | 3.0 | 4.1 | 6.0 |
| cracking | 1.84 | 1.84 | 1.9 | 2.06 | 2.3 | 3.8 | 1.78 |

While the invention has been described with what are presently considered the preferred embodiments, it is to be understood that the invention is not limited to the disclosed embodiments, but it is intended to cover various modifications of the plates, combinations of plates, and equivalent arrangements included within the scope of the appended claims.

The invention claimed is:

1. A process for alkylation of an aromatic hydrocarbon feedstream comprising:
   reacting a substantially linear olefin with an aromatic hydrocarbon feedstream in the presence of a catalyst under alkylation reaction conditions to produce alkyhas an effective diameter from about 0.05 mm to about 5 mm, and wherein the outer layer has a thickness from 10 to 300 microns.

2. The process of claim 1 wherein the binder is an inorganic metal oxide selected from the group consisting of alumina, silica, magnesia, titania, zirconia, and mixtures thereof.

3. The process of claim 1 where the alkylation conditions comprise a pressure from 1.4 MPa (203 psia) to 7 MPa (1015 psia), and a temperature from 50° C. to 200° C.

4. The process of claim 3 where the alkylation conditions comprise a pressure from 2 MPa (290 psia) to 3.5 MPa (507 psia), and a temperature from 80° C. to 175° C.

5. The process of claim 1 wherein the liquid hourly space velocity is from 0.1 to 30 hr$^{-1}$.

6. The process of claim 1 wherein the liquid hourly space velocity from 0.3 to 6 hr$^{-1}$.

7. The process of claim 1 wherein the aryl to monoolefin molar ratio is from 2.5:1 to 50:1.

8. The process of claim 7 wherein the aryl to monoolefin molar ratio is from 5:1 to 35:1.

9. The process of claim 1 wherein the substantially linear alpha olefin has from 8 to 15 carbon atoms.

* * * * *